United States Patent [19]

Bernstein et al.

[11] 4,027,038

[45] May 31, 1977

[54] COMPLEMENT INHIBITORS

[75] Inventors: Seymour Bernstein, New City, N.Y.; Robert Herman Lenhard, Paramus, N.J.

[73] Assignee: American Cyanamid Company, Stamford, Conn.

[22] Filed: May 10, 1976

[21] Appl. No.: 684,600

[52] U.S. Cl. .............................................. 424/315
[51] Int. Cl.² ...................................... A61K 31/185
[58] Field of Search ................................... 424/315

[56] References Cited

UNITED STATES PATENTS 3,897,434   7/1975   Katner ............................... 424/250

OTHER PUBLICATIONS

Wills et al., Biochem. J., 47, pp. 158–170, (1950).
Balaban et al., J. Chem. Soc., pp. 3068–3097, (1927).
Adams et al., J. Chem. Soc., pp. 3739–3744, (1956).
Jose et al., Chemical Abstracts 71:20472z, (1969).

*Primary Examiner*—Norman A. Drezin
*Attorney, Agent, or Firm*—Jack W. Richards

[57] ABSTRACT

Naphthalenedisulfonic acid ureides and their salts useful as complement inhibitors.

18 Claims, No Drawings

COMPLEMENT INHIBITORS

BACKGROUND OF THE INVENTION

The present invention resides in the concept of certain naphthalenedisulfonic acid ureides and their salts and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of sub-units designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Scientific American, 229, (No. 5), 54–66 (1973); Medical World News, Oct. 11, 1974, pp. 53–58; 64–66; Harvey Lectures, 66, 75–104 (1972); The New England Journal of Medicine, 287, 489–495; 545–549; 592–596; 642–646 (1972); The Johns Hopkins Med. J., 128, 57–74 (1971); and Federation Proceedings, 32, 134–137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389(1969).

A variety of substances have been disclosed as inhibiting the complement system, i.e., as complement inhibitors. For example, the compounds 3,3'-ureylenebis[6-(2- amino-8 -hydroxy-6-sulfo-1-naphthylazo)] benzenesulfonic acid tetrasodium salt (chlorazol fast pink), heparin, a heparin preparation and a sulphated dextran have been reported to have an anti-complementary effect, *British Journal of Experimental Pathology*, 33, 327–339 (1952), The compound 8,8'-ureylenebis [m-phenylcarbonylimino(4-methyl-m-phenylene) carbonylimino] di-1,3,5-naphthalenetrisulfonic acid, hexasodium salt (Suramin Sodium) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4-(3-phenylallyl)piperazines useful as complement inhibitors. U.S. Pat. No. 3,897,434 discloses certain pyrazolo [1,5-c]-quinazoline-5(6H)-ones as complement inhibitors. The compound, m-[m-(p-nitrophenylureido)-phenoxypropoxy]benzamide, is also a complement inhibitor, Immunology, 26, 819 (1974). Other chemical compounds having complement inhibiting activity are disclosed in, for example, *Journal of Medicinal Chemistry*, 12, 415–419; 902–905; 1049–1052; 1053–1056 (1969); *Canadian Journal of Biochemistry*, 47, 547–552 (1969); *The Journal of Immunology*, 93, 629–640 (1964); *The Journal of Immunology*, 104, 279–288 (1970); *The Journal of Immunology*, 106, 241–245 (1971); and *The Journal of Immunology*, 111, 1061–1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812 (1972); *Allergol, Et. Immunopath*, II, 163–168 (1974); and *J. Allergy Clin. Immunol.*, 53, No. 5, 298–302 (1974).

SUMMARY OF THE INVENTION

It has now been discovered that certain naphthalenedisulfonic acid ureides and their salts interact with the complement reaction sequence, thereby inhibiting complement activity in body fluids.

This invention is concerned with all pharmaceutically acceptable naphthalenedisulfonic acid ureides and their salts having complement inhibiting activity of general formula (I):

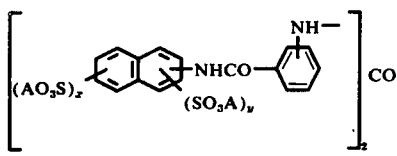

wherein $x$ is 1 or 2; $y$ is zero or 1; and A is hydrogen, sodium or potassium, with the proviso that A is identical in the same compound and $x$ is only 2 when $y$ is zero.

Of particular interest are those compounds which can be represented by general formula (II):

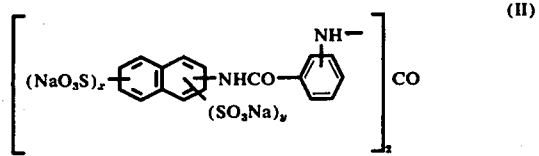

wherein $x$ is 1 or 2; and $y$ is zero or 1, with the proviso that $x$ is only 2 when $y$ is zero.

Typical compounds encompassed with formulae (I) and (II) include, for example, those of the formulae:

Of the compounds represented by the formulae, those compounds of most interest are the 1,5-disulfonic acid ureide (C2-substituted) compound, 2,2'-[ureylenebis(m-phenylenecarbonylimino)]di-1,5-naphthalenedisulfonic acid tetrasodium salt; the 3,6-disulfonic acid ureide (C1-substituted) compound, 4,4'-[ureylenebis(m-phenylenecarbonylimino)]di-2,7-naphthalenedisulfonic acid tetrasodium salt; the 4,8-disulfonic acid ureides (C1-substituted) compounds, 4,4'-[ureylenebis(p-phenylenecarbonylimino)]di-1,5-naphthalenedisulfonic acid tetrasodium salt and 4,4'-[ureylenebis(m-phenylenecarbonylimino)]di-1,5-naphthalenedisulfonic acid tetrasodium salt; and the 6,8-disulfonic acid ureides (C2- and C3-substituted) compounds, 6,6'-[ureylenebis(m-phenylenecarbonylimino)]di-1,3-naphthalenedisulfonic acid tetrasodium salt and 7,7'-[ureylenebis(m-phenylenecarbonylimino)]di-1,3-naphthalenesulfonic acid tetrasodium salt.

The following references describe compounds which are used in the method of this invention: *J. Chem. Soc.*, 3068 (1927); *J. Chem. Soc.*, 3739 (1956); *Biochem. J.*, 42, 109 (1948); *Biochem. J.*, 47, 158 (1950); and *Ann. Inst. Pasteur*, 38, 81 (1924).

Representative compounds encompassed within the method of treatment of this invention include, for example, 2,2'-[ureylenebis(m-phenylenecarbonylimino)]di-1,5-naphthalenedisulfonic acid tetrasodium salt; 4,4'-[ureylenebis(m-phenylenecarbonylimino)]di-2,7-naphthalenedisulfonic acid tetrasodium salt; 4,4'-[ureylenebis(p-phenylenecarbonylimino)]di-1,5-naphthalenedisulfonic acid tetrasodium salt; 4,4'-[ureylenebis(m-phenylenecarbonylimino)]di-1,5-naphthalenedisulfonic acid tetrasodium salt; 6,6'-[ureylenebis(m-phenylenecarbonylimino)]di-1,3-naphthalenedisulfonic acid tetraso- 1,5-Disulfonic Acid Ureide (C2-Substituted)

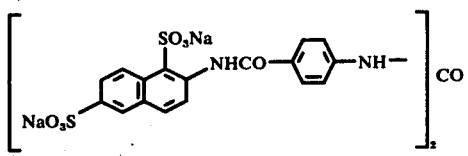

3,6-Disulfonic Acid Ureide (C1-Substituted)

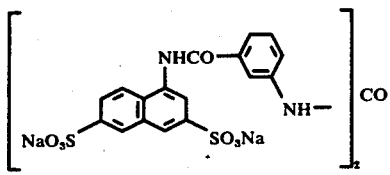

4,8-Disulfonic Acid Ureides (C1-Substituted)

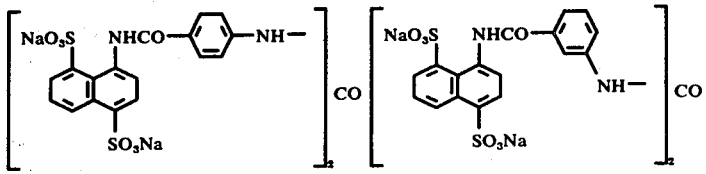

6,8-Disulfonic Acid Ureides (C2 and C3-Substituted)

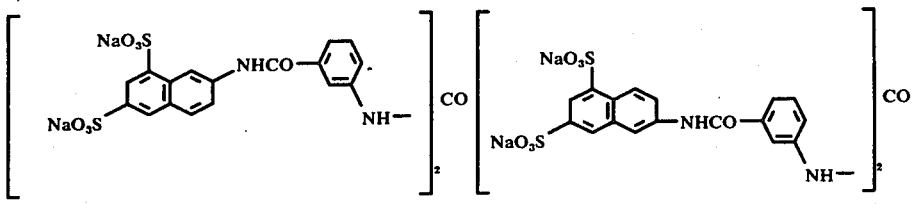

dium salt; and 7,7'-[ureylenebis(m-phenylenecarbonylimino)]di-1,3-naphthalenedisulfonic acid tetrasodium salt.

The compounds of the present invention can be prepared by acylation of the respective naphthylaminedisulfonic acid with m-nitrobenzoyl chloride followed by catalytic reduction and subsequent condensation of the respective amine with the appropriate substituted phenyl isocyanate; or by phosgenation of the respective amine. Acidification produces the free acid. A more explicit illustration of the reactions follows:

SCHOTTEN-BAUMANN ACYLATION

To a solution of the sodium salt of a naphthylaminedisulfonic acid in an appropriate amount of water, and 1N sodium -hydroxide is added m-nitrobenzoyl chloride. The mixture is shaken until no longer basic to test paper. Three additional equal portions of 1N sodium hydroxide are added, shaking between each addition until the solution is no longer basic. After the last portion of base is added, the reaction mixture is shaken for at least 30 minutes and then the still basic solution is acidified to Congo Red with concentrated hydrochloric acid. The reaction mixture is then copiously extracted with ether to remove the m-nitrobenzoic acid side product (by vacuum siphoning of the ethereal layer). The aqueous phase is then filtered to remove a small amount of the anhydride of m-nitrobenzoic acid and the filtrate is concentrated in vacuo at 50°–60° C until a solid is precipitated. After cooling to ambient temperature, the product is filtered and is washed with saturated saline solution, 50% ethyl alcohol, absolute ethyl alcohol and ether.

CATALYTIC REDUCTION

Treatment of a solution of the appropriate amount of the desired m-nitrobenzamide of naphthalenedisulfonic acid in 160–200 ml of water with 1.0–3.7 g of 10% palladium on carbon in a Parr apparatus under an initial hydrogen pressure of 42 pounds per square inch gives a theoretical uptake of hydrogen in 1¾ hours. The reaction mixture is filtered through diatomaceous earth and the catalyst is washed with water. The filtrate is concentrated under reduced pressure at 50°–60° C to low volume and is then diluted with a large volume of absolute ethanol. The precipitated product is collected and is washed with absolute ethyl alcohol.

PHOSGENATION

Phosgene is bubbled through a mechanically stirred solution of the desired aminobenzamide of naphthalenedisulfonic acid in the appropriate amount of water containing a theoretical quantity of sodium carbonate until the reaction mixture becomes acidic to Congo Red. An additional quantity of carbonate is cautiously added and the process is repeated until the reaction mixture is again acidic. It is then neutralized with an appropriate base and is concentrated in vacuo at 50°–60° C. On cooling to room temperature a solid is formed which is filtered and is washed with 80% ethyl alcohol, absolute ethyl alcohol and ether.

ACYLATION WITH ISOCYANATES

A solution of the appropriate amount of the desired m-aminobenzamide of naphthalenedisulfonic acid sodium salt in water is treated with a theoretical portion of the required isocyanate and is stirred vigorously for 6 hours at room temperature. The reaction mixture is diluted with additional water, is heated to approximately 95° C for 30 minutes and is filtered through diatomaceous earth and is washed with hot water. The filtrate is treated with sodium chloride while heating on the steam bath and is allowed to stand at room temperature overnight (lower temperature is required in some cases). The precipitate is collected and is boiled with absolute ethyl alcohol then is allowed to stand at room temperature for several days. The product is then filtered and washed with absolute ethyl alcohol and ether.

This invention is particularly concerned with a method of inhibiting the complement system in a body fluid, such as blood serum, which comprises subjecting body fluid complement to the action of an effective complement inhibiting amount of a compound encompassed with the formulae hereinabove. The method of use of this invention is also concerned with a method of inhibiting the complement system in a warm-blooded animal which comprises internally administering to said animal an effective complement inhibiting amount of a compound encompassed within the formulae hereinabove. Body fluid can include blood, plasma, serum, synovial fluid, cerebrospinal fluid, or pathological accumulations of fluid as pleural effusion, etc., containing complement.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin, etc.) and inflammatory states induced by the action of bacterial of lysosomal enzymes on the appropriate complement components as for exlample, inflammation following coronary occlusion. They may also be useful in the treatment of transplant rejection and as blood culture or transport mediums.

DETAILED DESCRIPTION OF THE INVENTION

The following examples will serve to illustrate the invention in more detail.

EXAMPLE 1

2-(m-Nitrobenzamido)-1,5-naphthalenedisulfonic acid disodium salt

A 48.5 g portion of 2-amino-1,5-naphthalenedisulfonic acid is suspended in 80 ml of water and 160 ml of 1N sodium hydroxide is added, then 60.0 g of m-nitrobenzoyl chloride is added all at once. The mixture is shaken for about 15 minutes and another 160 ml of 1N sodium hydroxide is added with shaking for ½ hour. The latter addition of sodium hydroxide and shaking is repeated two more times, then 100 ml of water is added and the mixture is acidified with 17 ml of concentrated hydrochloric acid. The resulting mixture is then copiously extracted with ether with the addition of 700 ml of water during the ether extraction. The ether is removed by vacuum siphoning and the aqueous solution is filtered. The filtrate is then concentrated in vacuo at 55°-60° C until formation of crystals. The material is then allowed to stand 48 hours at room temperature and the solid residue of fine feathery needles is broken up and is filtered. The residue is washed with two 100 ml portions of saturated saline solution and then is slurried with two 200 ml portions of 90% ethyl alcohol followed by 200 ml of absolute ethyl alcohol and two 300 ml portions of ether. The product is then dried at 120° C overnight to give 52.8 g of product. A 27.8 g portion of this material is dissolved in 110 ml of boiling water. The solution is then cooled to room temperature and the crystallized final product is filtered and is washed with a small amount of cold water then is dried at 120° C overnight.

EXAMPLE 2

2-(m-Aminobenzamido)-1,5-naphthalenedisulfonic acid disodium salt

A mixture of 25.0 g of 2-(m-(nitrobenzamido)-1,5-naphthalenedisulfonic acid disodium salt (prepared as in Example 1), 250 ml of water and 2.0 g of 10% palladium on charcoal is hydrogenated in a Parr shaker for 3½ hours at room temperature with an initial pressure of 42 pounds of hydrogen. During this time a total of 11.5 pounds of hydrogen is absorbed.

The mixture is heated to dissolve some precipitated product and is filtered hot to remove the catalyst. The filtrate is then evaporated to a small volume in vacuo at about 60° C and a copious amount of absolute ethyl alcohol is added. The product is collected by filtration, is washed with absolute alcohol and is oven dried overnight at 120° C.

EXAMPLE 3

4-(p-Nitrobenzamido)-1,5-naphthalenedisulfonic acid disodium salt

A 25.0 g portion of 4-amino-1,5-naphthalenedisulfonic acid sodium salt is suspended in 100 ml of water and 80 ml of 1N sodium hydroxide is added, then 31.0 g of p-nitrobenzoylchloride is added all at once. The mixture is shaken for about 15 minutes and another 80 ml of 1N sodium hydroxide is added with additional shaking. The latter addition of sodium hydroxide and shaking is repeated three more times with the incorporation of 50 ml of water and 25 ml of ether. The final solution remains basic after about 30 minutes of shaking and is then acidified with 20 ml of concentrated hydrochloric acid (which is indicated by a deep blue color to Congo Red test paper). The solution is then diluted to one liter with water and is then extracted with 500 ml of ether. The emulsified ether phase is removed by vacuum siphoning. The ether extraction is repeated 8 additional times with 250 ml portions of ether. The aqueous phase is neutralized with 5N sodium hydroxide and the insoluble fraction is removed by filtration and is washed with 100 ml of 80% ethyl alcohol followed by 100 ml of absolute ethyl alcohol. The washes are combined with the filtrate obtained above and the combined solution is evaporated in vacuo at 55°-60° C to about 500 ml. The solution is cooled to room temperature and the resultant crystalline material is collected by filtration and is washed consecutively with two 100 ml portions of 90% ethyl alcohol, 100 ml of absolute ethyl alcohol and two 100 ml portions of ether. The product of the example is then oven dried at 120° C overnight.

EXAMPLE 4

4-(p-Aminobenzamido)-1,5-naphthalenedisulfonic acid disodium salt

A mixture of 10.0 g of 4-p-nitrobenzamido-1,5-naphthalenedisulfonic acid disodium salt (prepared as in Example 3), 200 ml of water and 1.0 g of 10% palladium on charcoal is hydrogenated in a Parr shaker for 1½ hours at room temperature with an initial pressure of 46 pounds of hydrogen. During this time a total of 4.5 pounds of hydrogen is absorbed. The mixture is heated to dissolve some precipitated product and is filtered hot to remove the catalyst. The filtrate is then evaporated to a small volume in vacuo at about 60° C and a copious amount of absolute ethyl alcohol is added. The product is collected by filtration and is washed with absolute ethyl alcohol followed by ether. After air drying the material is oven dried at 120° C overnight.

EXAMPLE 5

4-(m-Nitrobenzamido)-1,5-naphthalenedisulfonic acid disodium salt

A 48.3 g portion of 4-amino-1,5-naphthalenedisulfonic acid sodium salt is suspended in 150 ml of water and 160 ml of 1N sodium hydroxide is added, then 60.0 g of m-nitrobenzoyl chloride is added all at once. The mixture is shaken for about 15 minutes or until no longer basic to test paper, then another 160 ml of 1N sodium hydroxide is added with additional shaking. The latter addition of sodium hydroxide and shaking is repeated two more times and when the mixture remains basic after ½ hour of shaking after the last portion is added the mixture is acidified to Congo Red with 15 ml of concentrated hydrochloric acid. Additional water is added to the mixture which is then copiously extracted with ether. The ether is removed by vacuum siphoning and the aqueous phase is filtered. The filtrate is neutralized and is concentrated at 55° C in vacuo until crystal formation then it is cooled to room temperature. The crystallized material is collected by filtration and is washed with 250 ml of saturated saline, then with two 150 ml portions of 50% ethyl alcohol followed by two 150 ml portions of absolute ethyl alcohol and two 150 ml portions of ethyl ether. The product of the example is then oven dried at 120° C overnight.

EXAMPLE 6

4-(m-Aminobenzamido)-1,5-naphthalenedisulfonic acid disodium salt

A mixture of 25.0 g of 4-(m-nitrobenzamido)-1,5-naphthalenedisulfonic acid disodium salt (prepared as in Example 5), 200 ml of water and 2.0 g of 10% palladium on charcoal is hydrogenated in a Parr shaker for 4 hours and 20 minutes at room temperature with an initial pressure of 42 pounds of hydrogen. During this time a total of 11.0 pounds of hydrogen is absorbed. The mixture is heated to dissolve some precipitated product and is filtered through diatomaceous earth to remove the catalyst. The filtrate is then evaporated to a small volume in vacuo at 55°-60° C until crystal formation. The material is then diluted with absolute ethyl alcohol and is triturated. The crystals are then collected by filtration and the product is washed first with two 100 ml portions of absolute ethyl alcohol followed by two 100 ml portions of ether. The product of the example is then oven dried overnight at 120° C.

EXAMPLE 7

2,2'-[Ureylenebis(m-phenylenecarbonylimino)]di-1,5-naphthalenedisulfonic acid tetrasodium salt To a stirred solution of 10.0 g of 2-(m-aminobenzamido)-1,5-naphthalenedisulfonic acid disodium salt prepared as in Example 2) and 22.4 g of anhydrous sodium carbonate in 250 ml of water is bubbled in phosgene at room temperature for 35 minutes before a thick translucent gel is formed. The gas diffuser is removed and stirring speed is increased considerably. The resulting mixture is changed to a white solid after about 20 minutes of stirring (at this point the mixture is not acid to Congo Red). The gas diffuser is reinserted and phosgenation is continued for an additional hour at room temperature then the acid mixture is neutralized with 12 ml of 3N sodium hydroxide. The mixture is then filtered over a 48 hour period to obtain a moist paste which is slurried with about 125-150 ml of 80% ethyl alcohol then is filtered and is oven dried at 120° C overnight to give the product of the example.

EXAMPLE 8

4,4'-[Ureylenebis(m-phenylenecarbonylimino)]di-2,7-naphthalenedisulfonic acid tetrasodium salt A 100 g portion of 4-amino-2,7-naphthalenedisulfonic acid technical grade (Freunds acid) is dissolved in one liter of hot water. The solution is boiled with activated charcoal for about 20 minutes and is filtered through diatomaceous earth. The filtrate is concentrated to about 600 ml and is diluted with 600 ml of absolute ethyl alcohol then is allowed to stand at room temperature for 36 hours. The mixture is filtered and the precipitate is washed with 200 ml of 50% ethyl alcohol followed by three 200 ml portions of absolute ethyl alcohol and several ether washes to give 66.0 g of the purified product.

A 36.3 g portion of above purified product is suspended in 80 ml of water and 120 ml of 1N sodium hydroxide is added, then 45.0 g of m-nitrobenzoyl chloride is added all at once plus an additional 120 ml of 1N sodium hydroxide. The mixture is shaken as well as possible for 10-15 minutes. The latter addition of sodium hydroxide and shaking is repeated 3 more times with a total shaking time of 2 hours. The mixture is then diluted with several hundred ml of water until clear, then is acified to Congo Red with 24 ml of concentrated hydrochloric acid. The aqueous phase is then extracted with six 150 ml portions of ether. The ether is removed by vacuum siphoning after each extraction. The aqueous phase is then filtered and the filtrate is neutralized with sodium hydroxide and allowed to stand overnight at room temperature. The insoluble fraction is filtered off and the filtrate is concentrated in vacuo at 65° C until crystals appear. The solution is cooled to room temperature and is allowed to stand overnight. The crystalline material is then filtered and is washed with two 100 ml portions of saturated saline solution, then two 100 ml portions of 50% ethyl alcohol followed by two 100 ml portions of absolute ethyl alcohol and two 150 ml portions of ether. This product is then oven dried at 120° C overnight to give 46.3 g of 4-(m-nitrobenzamido)-2,7-naphthalenedisulfonic acid disodium salt.

A 25.0 g portion of the preceding product, 250 ml of water and 2.0 g of 10% palladium on charcoal is hydrogenated in a Parr shaker for 2½ hours at room temperature with an initial pressure of 40 pounds of hydrogen. During this time a total of 12.8 pounds of hydrogen is absorbed.

The mixture is heated and then is filtered hot through diatomaceous earth to remove the catalyst. The filtrate is then evaporated to a small volume in vacuo at about 60° C and a copious amount of absolute ethyl alcohol is added. The product is collected by filtration, is washed with absolute alcohol and ether then is air dried and is finally oven dried at 120° C overnight to give 4-(m-aminobenzamido)-2,7-naphthalenedisulfonic acid disodium salt as an off-white to pink material.

To a stirred solution of 10.0 g of the preceding product and 44.5 g of anhydrous sodium carbonate in 250 ml of water is bubbled in phosgene at a slow to moderate rate at room temperature for 4½ hours. The resulting mixture is neutralized and is allowed to stand at room temperature for 48 hours then it is filtered and the precipitate is washed with two 50 ml portions of saturated saline solution and two 100 ml portions of 90% ethyl alcohol followed by 100 ml of absolute ethyl alcohol and two 100 ml portions of ether. The material is oven dried for one hour at 120° C then is dissolved in 200 ml of boiling water. The solution is cooled to room temperature and a moist gel is collected by filtration. The gel is added to 300 ml of 50% ethyl alcohol and is stirred for 2 hours then is filtered. The material is then washed by slurrying with 250 ml of 90% ethyl alcohol followed by 200 ml of absolute ethyl alcohol and two 150 ml portions of ether. The product of the example is then oven dried at 120° C overnight.

EXAMPLE 9

4,4'-[Ureylenebis(p-phenylenecarbonylimino)]di-1,3-naphthalenedisulfonic acid tetrasodium salt To a stirred solution of 10.0 g of 4-(p-aminobenzamido)-1,5-naphthalenedisulfonic acid disodium salt (prepared as in Example 4) and 22.7 g of anhydrous sodium carbonate in 250 ml of water is bubbled in phosgene for 30 minutes. An additional 22.7 g of sodium carbonate is added and the solution is phosgenated 30 minutes longer. Stirring is continued for 2 hours more then the solution is neutralized and is allowed to stand at room temperature. The fine white needles are collected by filtration in a sintered funnel. The product is slurried in the funnel with two 100 ml portions of 90% ethyl alcohol then is oven dried at 120° C overnight.

EXAMPLE 10

4,4'-[Ureylenebis(m-phenylenecarbonylimino)]di-1,3-naphthalenedisulfonic acid tetrasodium salt To a stirred solution of 10.0 g of 4-(m-aminobenzamido)-1,5-naphthalenedisulfonic acid disodium salt (prepared as in Example 6) and 22.4 g of anhydrous sodium carbonate in 250 ml of water is bubbled in phosgene for 1¼ hours, an additional 22.4 g of sodium carbonate is added and the solution is phosgenated 20 minutes longer. Stirring is continued and the resulting mixture is neutralized and is concentrated in vacuo at 55° C to about 150 ml. The hot solution is filtered and the filtrate is allowed to stand at room temperature overnight during which time a gelatinous solid is separated from the aqueous phase. This material is filtered and is pressed on the filter with a spatula to aid drying.

The gelatinous material is then triturated with 50 ml of methyl alcohol at ambient temperature and is filtered and washed with 25 ml of cold methyl alcohol. The product of the example is then oven dried at 120° C overnight.

EXAMPLE 11

6,6′-[Ureylenebis(m-phenylenecarbonylimino)]di-1,3-naphthalenedisulfonic acid tetrasodium salt A 36.3 g portion of 2-naphthylamine-5,7-disulfonic acid (amino-J-acid) is suspended in 80 ml of water and 120 ml of 1N sodium hydroxide is added, then 45.0 g of m-nitrobenzoyl chloride is added all at once. The mixture is shaken for about 15 minutes in a separatory funnel and another 120 ml of 1N sodium hydroxide is added with continued shaking for about 15 minutes. The latter addition of sodium hydroxide and shaking is repeated three more times. The solution is complete and is slightly basic after the last addition. The mixture is then acidified with concentrated hydrochloric acid to Congo Red test paper and is copiously extracted with ether about 7 times. The ether is removed by vacuum siphoning after each extraction. The separated aqueous phase is neutralized with sodium hydroxide and is concentrated in vacuo at 60°–65° C until a precipitate begins to form. The material is then allowed to stand at room temperature overnight and the solid residue is broken up and filtered. The residue is then washed with saturated sodium chloride followed by 50% ethyl alcohol then is oven dried at 120° C overnight to give 6-m-(nitrobenzamido)-1,3-naphthalenedisulfonic acid disodium salt.

A mixture of 25.0 g of the compound directly above, 200 ml of water and 2.0 g of 10% palladium on charcoal is hydrogenated in a Parr shaker for 4 hours at room temperature with an initial pressure of 42 pounds of hydrogen during which time 12.5 pounds of hydrogen is absorbed. The mixture is heated to dissolve some precipitated product and is filtered through diatomaceous earth to remove the catalyst. The filtrate is then evaporated to a small volume in vacuo at 55°–60° C until formation of a precipitate. The material is then diluted with absolute ethyl alcohol and is triturated. The precipitate is then collected by filtration and is washed with absolute alcohol then is oven dried at 120° C overnight to yield 21.37 g of 6-(m-aminobenzamido)-1,3-naphthalenedisulfonic acid disodium salt.

A 10.0 g portion of the preceding compound and 22.4 g of anhydrous sodium carbonate is dissolved in 250 ml of water stirred with a mechanical stirrer. Phosgene is bubbled in for one hour and twelve minutes and the mixture which is acid to Congo Red indicator paper is neutralized with 4–5 g of sodium carbonate. The mixture is then concentrated in vacuo at 50°–55° C to about 160 ml with formation of a precipitate which is collected by filtration and is set aside. The filtrate is concentrated in vacuo until crystals appear, then this precipitate is collected and is combined with the material set aside above. The combined mass is triturated with absolute ethyl alcohol and is filtered. The filtrate is discarded and the insoluble material is dissolved in 20 ml of hot water and is diluted with 60 ml of absolute alcohol and the flask is scratched with a glass rod to induce crystal formation. The material formed is filtered and is washed with 80% ethyl alcohol. The material is then dissolved in 50 ml of hot water and 150 ml of absolute ethyl alcohol and is allowed to stand for 4 days. The liquid is decanted and the crystalline solid is slurried with 50 ml of 80% ethyl alcohol and is essentially all dissolved. Recrystallization is accomplished by addition of about 100 ml of absolute alcohol. This precipitate is filtered and is washed with absolute alcohol to give the product of the example which is oven dried at 120° C overnight.

EXAMPLE 12

7,7′-[Ureylenebis(m-phenylenecarbonylimino)]di-1,3-naphthalenedisulfonic acid tetrasodium salt A 52.2 g portion of 7-amino-1,3-naphthalenedisulfonic acid monosodium salt (technical) is suspended in 80 ml of water and 160 ml of 1N sodium hydroxide is added, then 60.0 g of m-nitrobenzoyl chloride is added all at once (a large lump of crystalline solid is separated on addition of the acid chloride). The mixture is diluted with an additional 80 ml of water and a second 160 ml portion of 1N sodium hydroxide is added after brief initial shaking. Shaking is continued and the latter addition of sodium hydroxide and shaking is repeated two more times with intermitent attempt at breaking up any crystalline lumps with a spatula. The resulting mixture is shaken at least one hour after the final base treatment. Since complete solution is not attained, eight 150 ml portions of water are added then two 500 ml portions still without complete solution. The material is allowed to stand overnight and a gel is formed which is further diluted with water and is broken up with a spatula. The mixture is then acidified with 17 ml of concentrated hydrochloric acid and is copiously extracted with ether. The ether is removed after each extraction by vacuum siphoning. The gel is filtered over a period of 2 days in two funnels. The residue is combined and dissolved in boiling water then is filtered. The filtrate (about 710 ml) is diluted with an equal amount of 3A alcohol and is allowed to stand at room temperature overnight. The resulting precipitate is filtered and is washed with several 100 ml portions of 50% ethyl alcohol then is slurried twice with 250 ml portions of absolute ethyl alcohol and finally with two 250 ml portions of ether to give 7-(m-nitrobenzamido)-1,3-naphthalenedisulfonic acid disodium salt which is oven dried at 120° C.

A 25.0 g portion of the compound above is dissolved in 210 ml of hot water in a Parr shaker, the solution is cooled to room temperature and a 2.0 g portion of 10% palladium catalyst on charcoal is added. The air is evacuated and the shaker is flushed with hydrogen several times. The starting material forms a gel which is hydrogenated at room temperature and an initial pressure of 40.5 pounds of hydrogen. Eventually the gel is broken and shaking proceeds normally. The hydrogenation is carried out for a period of 6 hours during which time 11.5 pounds of hydrogen is absorbed. The mixture is then heated to dissolve some precipitated product and is filtered through diatomaceous earth to remove the catalyst then is washed with water. The filtrate is evaporated to a small volume in vacuo at 55° C until formation of a precipitate. The material is then diluted with absolute ethyl alcohol and is filtered and washed with absolute ethyl alcohol and ether. The material is then oven dried at 120° C overnight. The dried product is dissolved in 100 ml of boiling water and 100 ml of absolute ethyl alcohol is added. The solution is evaporated in vacuo until crystals appear, then is diluted with a large volume of absolute alcohol and is filtered and washed with absolute ethyl alcohol to give 7-(m-aminobenzamido)-1,3-naphthalenedisulfonic acid disodium salt.

A 10.0 g portion of the preceding compound and 22.4 g of anhydrous sodium carbonate is dissolved in 250 ml of water stirred with a mechanical stirrer. Phosgene is bubbled in for 1½ hours and the mixture is neutralized with 5N sodium hydroxide and is filtered. The collected precipitate is slurried in the funnel with two 100 ml portions of 80% ethyl alcohol then is oven dried at 120° C for 48 hours to give the product of the example.

EXAMPLE 13

Preparation of Compressed Tablet

| Ingredient | mg/Tablet |
| --- | --- |
| Active Compound | 0.5–500 |
| Dibasic Calcium Phosphate N.F. | qs. |
| Starch USP | 40 |
| Modified Starch | 10 |
| Magnesium Stearate USP | 1–5 |

EXAMPLE 14

Preparation of Compressed Tablet - Sustained Action

| Ingredient | mg/Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 15

Preparation of Hard Shell Capsule

| Ingredient | mg/Capsule |
| --- | --- |
| Active Compound | 0.5–500 |
| Lactose, Spray Dried | qs |
| Magnesium Stearate | 1–10 |

EXAMPLE 16

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 17

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 18

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |

-continued

Preparation of Oral Suspension (Syrup)

| Ingredient | % W/V |
| --- | --- |
| Liquid Sugar | 75.0 |
| Purified Water qs ad | 100.0 |

EXAMPLE 19

Preparation of Injectable Solution

| Ingredient | % W/V |
| --- | --- |
| Active Compound | 0.05–5 |
| Benzyl Alcohol NF | 0.9 |
| Water for Injection | 100.0 |

EXAMPLE 20

Preparation of Injectable Oil

| Ingredient | % W/V |
| --- | --- |
| Active Compound | 0.05–5 |
| Benzyl Alcohol | 1.5 |
| Sesame Oil qs ad | 100.0 |

EXAMPLE 21

Preparation of Intra-Articular Product

| Ingredient | Amount |
| --- | --- |
| Active Compound | 2–20 mg |
| Na Cl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 22

Preparation of Injectable Depo Suspension

| Ingredient | % W/V |
| --- | --- |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

The compounds of this invention may be administered internally, e.g., orally or parenterally, such as, intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of representative compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor). This test determines the ability of the late components of human complement (C3–C9) to lyse EAC 142 in the presence of appropriate dilutions of the test compound. An active inhibitor protects EAC 142 from lysis by human C3–C9; (ii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or other, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

Table I shows that the compounds of the invention possess complement inhibiting activity in one or more of the tests.

TABLE I

| | BIOLOGICAL ACTIVITIES | | | | |
| --- | --- | --- | --- | --- | --- |
| | | Assay Results | | | |
| | In Vitro | | | In Vivo | |
| Compound | 026* | 035 | 036 | Forssman | % Reduction Complement |
| 2,2'-[Ureylenebis(m-phenylenecarbonylimino)]di-1,5-naphthalenedisulfonic acid tetrasodium salt | NEG | 1 | 1 | 10 | −18 |
| 4,4'-[Ureylenebis(m-phenylenecarbonylimino)]di-2,7-naphthalenedisulfonic acid tetrasodium salt | 3** | NEG | NEG | 0 | +4 |
| 4,4'-[Ureylenebis(p-phenylenecarbonylimino)]di-1,5-naphthalenedisulfonic acid tetrasodium salt | NEG | NEG | NEG | 12 | +58 |

TABLE I-continued

| | BIOLOGICAL ACTIVITIES | | | | |
| --- | --- | --- | --- | --- | --- |
| | | Assay Results | | | |
| | | In Vitro | | In Vivo | |
| Compound | 026* | 035 | 036 | Forssman | % Reduction Complement |
| 4,4'-[Ureylenebis(m-phenylenecarbonyl-imino)]di-1,5-naphthalenedisulfonic acid tetrasodium salt | 2 | NEG | NEG | 10 | −18 |
| 7,7'-[Ureylenebis(m-phenylenecarbonyl-imino)]di-1,3-naphthalenedisulfonic acid tetrasodium salt | 3 | 1 | 1 | 8 | −33 |

*Tests identified by code herein
**Numbers represent activity in wells, a serial dilution assay, higher well number indicates higher activity. The serial dilutions are two-fold.

We claim:

1. A method of inhibiting the complement system in a body fluid which comprises subjecting said body fluid to the action of an effective complement inhibiting amount of a compound of the formula:

$$\left[ (AO_3S)_x \overset{NH-}{\underset{(AO_3S)_y}{\bigodot\bigodot}} NHCO-\bigodot \right]_2 CO$$

wherein $x$ is 1 or 2; $y$ is zero or 1; and A is hydrogen, alkali metal or alkaline earth, with the proviso that A is identical in the same compound and $x$ is only 2 when $y$ is zero.

2. A method of inhibiting the complement system in a body fluid which comprises subjecting said body fluid to the action of an effective complement inhibiting amount of a compound of the formula:

$$\left[ (NaO_3S)_x \overset{NH-}{\underset{(SO_3Na)_y}{\bigodot\bigodot}} NCO-\bigodot \right]_2 CO$$

wherein $x$ is 1 or 2; and $y$ is zero or 1, with the proviso that $x$ is only 2 when $y$ is zero.

3. The method according to claim 2 wherein the compound is 2,2'-[ureylenebis(m-phenylcarbonylimine)]di-1,5-naphthalenedisulfonic acid tetrasodium salt.

4. The method according to claim 2 wherein the compound is 4,4'-[ureylenebis(m-phenylenecarbonylimino)]di-2,7-naphthalenedisulfonic acid tetrasodium salt.

5. The method according to claim 2 wherein the compound is 4,4'-[ureylenebis(p-phenylenecarbonylimino)]di-1,5-naphthalenedisulfonic acid tetrasodium salt.

6. The method according to claim 2 wherein the compound is 4,4'-[ureylenebis(m-phenylenecarbonylimino)]di-1,5-naphthalenedisulfonic acid tetrasodium salt.

7. The method according to claim 2 wherein the compound is 6,6'-[ureylenebis(m-phenylenecarbonylimino)]di-1,3-naphthalenedisulfonic acid tetrasodium salt.

8. The method according to claim 2 wherein the compound is 7,7'-[ureylenebis(m-phenylenecarbonylimino(]di-1,3-naphthalenedisulfonic acid tetrasodium salt.

9. The method according to claim 2 wherein the body fluid is blood serum.

10. A method of inhibiting the complement system in a warm-blooded animal which comprises internally administering to said animal an effective complement inhibiting amount of a compound to the formula:

$$\left[ (AO_3S)_x \overset{NH-}{\underset{(SO_3A)_y}{\bigodot\bigodot}} NHCO-\bigodot \right]_2 CO$$

wherein $x$ is 1 or 2; $y$ is zero or 1; and A is hydrogen, alkali metal or alkaline earth, with the proviso that A is identical in the same compound and $x$ is only 2 when $y$ is zero.

11. A method of inhibiting the complement system in a warm-blooded animal which comprises internally administering to said animal an effective complement inhibiting amount of a compound of the formula:

$$\left[ (NaO_3S)_x \overset{NH-}{\underset{(SO_3Na)_y}{\bigodot\bigodot}} NCO-\bigodot \right]_2 CO$$

wherein $x$ is 1 or 2; and $y$ is zero or 1, with the proviso the $x$ is only 2 when $y$ is zero.

12. The method according to claim 11 wherein the compound is administered intra-articularly.

13. The method according to claim 11 wherein the compound is 2,2'-[ureylenebis(m-phenylenecarbonylimino)[1,5-naphthalenedisulfonic acid tetrasodium salt.

14. The method according to claim 11 wherein the compound is 4,4'-[ureylenebis(m-phenylenecarbonylimino)]di-2,7-naphthalenedisulfonic acid tetrasodium salt.

15. The method according to claim 11 wherein the compound is 4,4'-[ureylenebis(p-phenylenecarbonylimino)]di-1,5-naphthalenedisulfonic acid tetrasodium salt.

16. The method according to claim 11 wherein the compound is 4,4'-[ureylenebis(m-phenylenecarbonylimino)]di-1,5-naphthalenedisulfonic acid tetrasodium salt.

17. The method according to claim 11 wherein the compound is 6,6'-[ureylenebis(m-phenylenecarbonylimino)]di-1,3-naphthalenedisulfonic acid tetrasodium salt.

18. The method according to claim 11 wherein the compound is 7,7'[ureylenebis(m-phenylenecarbonylimino)]di-1,3-naphthalenedisulfonic acid tetrasodium salt.

* * * * *

UNITED STATES PATENT OFFICE
CERTIFICATE OF CORRECTION

Patent No. 4,027,038   Dated May 31, 1977

Inventor(s) Seymour Bernstein and Robert Herman Lenhard

It is certified that error appears in the above-identified patent and that said Letters Patent are hereby corrected as shown below:

Claim 3, lines 45-46, left-hand side,
 change "phenylcarbonylimine"
 to --phenylenecarbonylimino--

Claim 8, line 66, left-hand side,
 change "("
 to --)--

Claim 13, line 47, right-hand side,
 change "bonylimino)[1,5-naphthalenedisulfonic"
 to --bonylimino)]di-1,5-naphthalenedisulfonic--

Claim 18, line 66, right-hand side,
 change "7,7'[ureylenebis"
 to --7,7'-[ureylenebis--

Signed and Sealed this thirtieth Day of August 1977

[SEAL]

Attest:

RUTH C. MASON
*Attesting Officer*

C. MARSHALL DANN
*Commissioner of Patents and Trademarks*